United States Patent [19]

Flanagan et al.

[11] Patent Number: 5,539,138
[45] Date of Patent: Jul. 23, 1996

[54] HIGH AFFINITY CHELATES CONTAINING ISOTHIOCYANATE GROUPS, USEFUL FOR COUPLING WITH PEPTIDES AND PROTEINS

[75] Inventors: Richard J. Flanagan, St. Lazare; Keith T. Hogan, Dorval; Jean-Marc Dufour, Pierrefonds; F. Peter Charleson, Kirkland, all of Canada

[73] Assignee: Merck Frosst Canada, Inc., Kirkland, Canada

[21] Appl. No.: 281,905

[22] Filed: Jul. 28, 1994

[51] Int. Cl.⁶ .................................................. C07C 331/28
[52] U.S. Cl. ............................................................ 558/17
[58] Field of Search ........................................ 558/13, 17

[56] References Cited

U.S. PATENT DOCUMENTS

| | | | |
|---|---|---|---|
| 3,313,779 | 4/1967 | White | 260/59 |
| 4,069,249 | 1/1978 | Gaudette et al. | 260/519 |
| 5,057,302 | 10/1991 | Johnson et al. | 424/1.1 |
| 5,101,041 | 3/1992 | Troutner et al. | 548/518 |
| 5,227,474 | 7/1993 | Johnson et al. | 534/558 |
| 5,248,764 | 9/1993 | Flanagan et al. | 530/324 |

OTHER PUBLICATIONS

Mathias et al., Nucl. Med. Biol. vol. 15, No. 1, pp. 69–81 (1988).
Mathias et al., Inorg. Chem., 29, pp. 1475–1480 (1990).
Mathias et al., Bioconjugate Chem., 1, pp. 204–211 (1990).
L'Eplattenieer et al., J. Amer. Chem. Soc., vol. 89(4), pp. 837–843 (1967).
Pitt et al., J. Med. Chem., vol. 29, pp. 1231–1237 (1986).

*Primary Examiner*—Johann Richter
*Assistant Examiner*—Laura R. Cross
*Attorney, Agent, or Firm*—J. Eric Thies; David L. Rose

[57] ABSTRACT

The ligands HBED-SCN, HBPD-SCN, and HTDD-SCN are provided which have enhanced ease of reaction with peptides or proteins and which are suitable for chelating with radioisoptopes, especially Indium-$^{111}$ and Gallium-$^{67}$.

1 Claim, No Drawings

HIGH AFFINITY CHELATES CONTAINING ISOTHIOCYANATE GROUPS, USEFUL FOR COUPLING WITH PEPTIDES AND PROTEINS

BACKGROUND OF THE INVENTION

Previously, chelates have been attached to peptides and proteins by means of amide bonds derived from the use of active esters and anhydrides (e.g. DTPA-anhydride). The problem with this approach is that the reaction conditions must be partially non-aqueous to avoid hydrolysis of the active ester or anhydride and many peptides/proteins are damaged by these conditions. In this invention, the problem is solved by means of chelates containing isothiocyanate groups which have higher affinity and which allow simpler coupling to peptides and proteins, e.g., at pH 8.5 in aqueous solutions. The coupling chemistry is simple and stoichiometric. The chelates are based on the hydroxybenzylethylenediamine-diacetic acid (HBED), hydroxybenzylpropylenediamine-diacetic acid (HBPD) and hydroxybenzylethylenetriamine-diacetic acid (HTDD) nucleus which offer greater affinity for $^{111}$In and $^{67}$Ga diethylene-triamine pentacetic acid (DTPA) chelates.

SUMMARY OF THE INVENTION

This invention describes a series of high affinity chelates or "ligands" which can easily be attached to peptides and proteins by means of an isothiocyanate linkage and are suitable for radiopharmaceutical metallic isotopes (e.g. $^{111}$In, $^{67}$Ga).

These compounds are HBED-SCN, HBPD-SCN, and HTDD-SCN, or the HBED, HBPD, and HTDD compounds having isothiocyanate groups.

These compounds have the following structures:

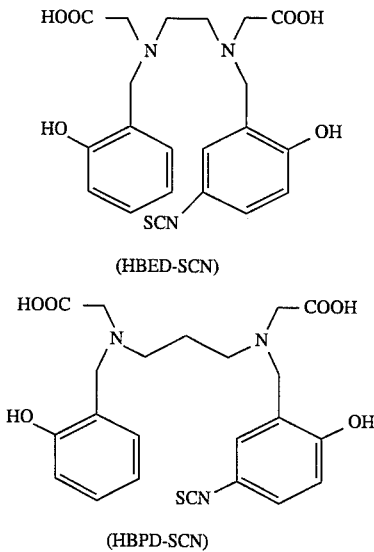

(HBED-SCN)

(HBPD-SCN)

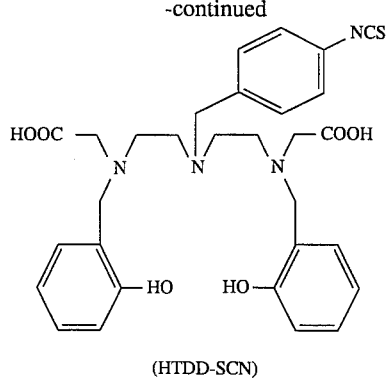

(HTDD-SCN)

These compounds are prepared by reacting an appropriate p-NO$_2$ phenyl-containing compound with the amine-diacetic acid intermediate; followed by reduction to the amino group using hydrogen gas on Pd/C catalyst, and finally forming the isothiocyanate group by treatment with thiophosgene in a solvent such as methylene chloride.

Following preparation of the isothiocyanate group on the desired nucleus. The ligand is coupled with any of the desired peptides or proteins, and then chelated with the appropriate radiolabelling agent.

The preferred peptide or protein to be used includes natural and synthetic somatostatin and analogues, atrial natriuretic factor peptides, fibrin binding domain peptides, and monoclonal antibodies or fragments thereof, F(ab)$_2$, Fab, Fv regions; oxytocin; substance P; vasopression; as well as any amino group containing peptidomimetics.

The preferred radio isotope is one of those of Indium or Gallium, especially Indium-$^{111}$ and Gallium-$^{67}$.

Others are Yltrium-$^{90}$, Gallium-$^{68}$, and Samarium-$^{152}$.

The reaction between the ligand/peptide compound and the detectable element is carried out using known methods, preferably at a pH at which the peptide is stable.

An alterative method of preparing the radio labelled peptide linked to the ligands of this invention first links together the chelating ligand complexed with the detectable element, and then the peptide in protected or unprotected form.

The same reaction may be performed with a chelating agent complexed with a non-detectable metal ion and then in the resulting complexed peptide the metal ion may be replaced by the desired detectable element.

Compounds can also be produced by linking together the chelating ligand complexed with the detectable element, and a peptide fragment comprising at least one amino acid in protected or unprotected form and then continuing the peptide synthesis step by step until the final peptide sequence is obtained and if desired removing at least one protecting group which is present. Instead of the detectable element the chelating agent may be complexed with a non detectable metal and this metal may then be replaced by the detectable element in the resulting complexed peptide.

The final products of this invention are useful either as an imaging agent, e.g., visualization of the particular (peptide) receptor positive tumors and metastases when complexed with a paramagnetic, a γ-emitting metal ion or a positron-emitting radionuclide, or as a radiopharmaceutical for the treatment in vivo of (peptide) receptor positive tumors and metastases when complexed with α or β-radionuclide, as indicated by standard tests.

The particular radioisotope chosen is relevant to the organ or system to be radioimaged. For instance, in the last few years a high incidence of somatostatin receptors has been demonstrated in a variety of human tumors, e.g., pituitary tumors, central nervous system tumors, breast tumors, gastoenteropancreatic tumors and their metastases. Some of them are small or slow-growing tumors which are difficult to precisely localize by conventional diagnosis methods, but in vitro visualization of somatostatin receptors has been performed through autoradiography of tumoral tissues using radioiodinated somatostatin analogues.

The final products of this invention when used as imaging agents may be administered parenterally, preferably intravenously, e.g., in the form of injectable solutions or suspensions, preferably in a single injection. The appropriate dosage will of course vary depending upon, for example, the precise chelating ligand and the type of detectable element used, e.g., the radionuclide. A suitable dose to be injected is in the range to enable imaging by photoscanning procedures known in the art. It may advantageously be administered in a dose having a radioactivity of from 0.1 to 50 mCi, preferably 0.1 to 30 mCi, more preferably 0.1 to 20 mCi. An indicated dosage range may be of from 1 to 200 μg product labelled with 0.1 to 50 mCi, preferably 0.1 to 30 mCi, e.g., 3 to 15 mCi, γ-emitting radionuclide, depending on the γ-emitting radionuclide used; e.g., with IN-111, it is preferred to use a radioactivity in the lower range.

The enrichment in the tumorigenic sites with the products may be followed by the corresponding imaging techniques, e.g., using nuclear medicine imaging instrumentation, for example a scanner, γ-camera, rotating γ-camera, each preferably computer assisted; PET-scanner (Positron emission tomography); MRI equipment or CAT scanning equipment.

These products can also be used for in vivo treatment of peptide receptor positive tumors and metastases in a subject in need of such a treatment which comprises administering to said subject a therapeutically effective amount of the product.

Dosages employed in practicing the therapeutic method of the present invention will of course vary depending e.g., on the particular condition to be treated, for example the volume of the tumor, the particular product employed, for example the half-life of the product in the rumor, and the therapy desired. In general, the dose is calculated on the basis of radioactivity distribution to each organ and on observed target uptake. For example, the product may be administered at a daily dosage range having a radioactivity of from 0.1 to 3 mCi/kg body weight, e.g., 1 to 3 mCi, preferably 1 to 1.5 mCi/kg body weight. An indicated daily dosage range is of from 1 to 200 μg ligand labelled with 0.1 to 3 mCi/kg body weight, e.g., 0.1 to 1.5/kg body weight α- or β-emitting radionuclide, conveniently administered in divided doses up to 4 times a day.

These products may be administered by any conventional route, in particular parenterally, e.g., in the form of injectable solutions or suspensions. They may also be administered advantageously by infusion, e.g., an infusion of 30 to 60 min. Depending on the site of the tumor, they may be administered as close as possible to the tumor site, e.g., by means of a catheter. The mode of administration selected may depend on the dissociation rate of the product used and the excretion rate.

These products may be administered in free form or in pharmaceutically acceptable form, such as salts which may be prepared in conventional manner and exhibit the same order of activity as the free compounds.

The products for use in the method of the present invention may preferably be prepared shortly before the administration to a subject, i.e., the radiolabelling with the desired detectable metal ion, particularly the desired α-, β- or γ-radionuclide, may be performed shortly before the administration.

They are then suitable for imaging or treating tumors such as pituitary, gastroenteropancreatic, central nervous system, breast, prostatic, ovarian or colonic tumors, small cell lung cancer, paragangliomas, neuroblastomas, pheochromocytomas, medullary thyroid carcinomas, myelomas, etc. and metastases thereof, as well as lymphomas.

According to a further aspect of the invention, there is provided:

a pharmaceutical composition comprising the radiolabelled product of the invention in free or in pharmaceutically acceptable salt form, together with one or more pharmaceutically acceptable carders or diluents therefor; or a pharmaceutical composition comprising a chelate-peptide product according to the invention in free or in pharmaceutically acceptable salt form, together with one or more pharmaceutically acceptable carders or diluents therefor.

Such compositions may be manufactured in conventional manner.

A composition according to the invention may also be presented in separate package with instructions for mixing the chelate-peptide product with the metal ion and for the administration of the resulting radiolabelled product. It may also be presented in twin-pack form, that is, as a single package containing separate unit dosages of the ligand and the detectable metal ion with instructions for mixing them and for administration of the product. A diluent or carder may be present in the unit dosage forms.

This invention is illustrated by the following examples.

Synthesis of HBED-SCN

Preparation of N-(2-hydroxybenzyl), N'-acetylethylenediamine, (4)

A: N-(2-hydroxybenzylidene), N'-acetylethylenediamie (3)

Salicylaldehyde 1, 3.2 mL (0.030 mole), was dissolved in 25 mL of dry benzene. To this solution N-acetylethylenediamine 2, 3.06 g (0.030 mole), dissolved in 50 mL of dry benzene and 5 mL of methanol was slowly added. A Dean-Stark apparatus and a condenser were installed to the round bottom flask then the reaction mixture was heated to reflux for 48 hours. The solvent was removed under vacuum and the residue was washed with diethyl ether. After it was vacuum dried at room temperature and 0.1 mm Hg for 18 hours, 6.11 g of the yellow Schiff base 3 was obtained.

$^1$H NMR (in CDCl$_3$): δ8.25 (s,1H,—CH=N—), 7.22 (ddd, J=2, 7 and 8Hz,1H,H$_4$—Ar), 7.16 (dd, J=2 and 8Hz, 1H,H$_6$—Ar), 6.85 (d, J=8Hz,1H,H$_3$—Ar), 6.79 (td, J=1 and 7Hz,1H,H$_5$—Ar), 5.86 (bs, 1H,NHCOCH$_3$), 3.62 (t, J=6Hz, 2H,—CH=N—CH$_2$—CH$_2$—NHCOCH$_3$), 3.46 (td, J=5 and 6Hz,2H,—CH=N—CH$_2$—CH$_2$—NHCOCH$_3$) and 1.87 (s,3H,—NHCOCH$_3$)ppm. $^{13}$C NMR (in CDCl$_3$): 170.2, 166.3, 160.7, 132.3, 131.3, 118.6, 116.8, 58.7, 40.2 and 23.1ppm. MS (EI; m/z): 206(43,M$^+$), 207(6,M$^+$+1), 147(27), 135(22), 134(72), 132(46), 118(44), 107 (100), 78(24), 77(52) and 51(28).

B: N-(2-hydroxybenzyl), N'-acetylethylenediamine, (4)

3.982 g (19.3 mmol) of the Schiff base 3 was dissolved in 100 mL of ethanol, to which 0.366 g (9.7 mmol) of sodium borohydride was added potionwise. It was stirred at room temperature for 17 hours. The solvent was removed by distillation under reduced pressure. To the yellow oil which remained was added 250 mL of water and the product was extracted four times with methylene chloride (220 mL). The organic extracts were combined and decolorized with 4.4 g of activated charcoal. The mixture was warmed for 10 min. After filtration a nearly colorless methylene chloride solution was obtained. This solution was dried with anhydrous magnesium sulfate, filtered and the solvent removed under reduced pressure to yield 2.92 g of N-(2-hydroxybenzyl), N'-acetylethylenediamine 4 as a light yellow oil.

$^1$H NMR (in CDCl$_3$): $\delta$7.17 (td,J=2 and 7Hz, 1H,H$_4$—Ar), 6.99 (d, J=7Hz, 1H,H$_6$—Ar), 6.82 (d,J=7Hz, 1H,H$_3$—Ar), 6.78 (td,J=1 and 7Hz, 1H, H$_5$—Ar), 5.81 (bs,1H,—NHCOCH$_3$), 4.01 (s,2H,Ar—CH$_2$—NH—), 3.40 (q, J=6Hz, 2H,—NH—CH$_2$—CH$_2$—NHCOCH$_3$), 2.81 (t,J=6Hz, 2H,—NH—CH$_2$—CH$_2$—NHCOCH$_3$) and 1.99 (s,3H,—NHCOCH$_3$) ppm. $^{13}$C NMR (in DMSO-d$_6$): 171.6, 155.4, 131.3, 130.5, 119.3, 117.2, 115.0, 46.0, 45.5, 35.0 and 22.1 ppm. MS (EI; m/z): 208(24,M$^+$), 209(6,M$^+$+1), 149(23), 136(57), 122(32), 108(15), 107(100), 78(11), 77(25).

Hydrolysis of N-(2-hydroxybenzyl), N'-acetylethylenediamine, (4)

N-(2-hydroxybenzyl), N'-acetylethylenediamine 4 (20.83 g; 0.1 mole) was dissolved in 200 mL of 6 N hydrochloric acid and this solution was refluxed for 24 hours. After the solvent was evaporated under vacuum, the residue was dissolved with the minimum volume of water and the pH was brought to about 8 with 5% sodium hydroxide. Then the mixture was extracted with ethyl acetate (3×200 mL). The combined extracts were dried with magnesium sulfate, filtered and evaporated to dryness to yield 14.73 g of N-(2-hydroxybenzyl)ethylenediamine 5, as a brownish oil.

$^1$H NMR (in CDCl$_3$): $\delta$7.07 (td,J=2 and 8Hz,1H,H$_4$—Ar), 6.91 (dd, J=1 and 7Hz, 1H,H$^6$—Ar), 6.73 (d,J=8Hz,1H, H$_3$—Ar), 6.69 (td,J=2 and 7Hz,1H,H$_5$—Ar), 4.07 (bs,3H), 3.86 (s,2H,Ar—CH$_2$—NH—), 2.73 (t,J=6Hz, 2H,Ar—CH$_2$—NH—CH$_2$—CH$_2$—NH$_2$) and 2.57 (t,J=6Hz,2H,Ar—CH$_2$—NH—CH$_2$—CH$_2$—NH$_2$) ppm. Preparation of N-(2-hydroxy-5-nitrobenzyl), N'-(2-hydroxybenzyl)ethylenediamine, (8)

A: N-(2-hydroxy-5-nitrobenzylidene), N'-(2-hydroxybenzyl)ethylenediamine, (7)

N-(2-hydroxybenzyl)ethylenediamine 5, 1.66 g (0.01 mole), was dissolved in 25 mL of dry benzene. To this solution 5-nitrosalicylaldehyde 6, 1.67 g (0.01 mole), dissolved in 50 mL of dry benzene and a few drops of methanol was slowly added. A Dean-Stark apparatus and a condenser were installed to the round bottom flask then the reaction mixture was refluxed for 24 hours. The solvent was removed under vacuum and the residue was washed with ether. After it was vacuum dried at room temperature and 0.1 mm Hg for 18 hours, and the yellow Schiff base 7 (2.297 g) was reduced without further purification.

B: N-(2-hydroxy-5-nitrobenzyl), N'-(2-hydroxybenzyl) ethylenediamine, (8)

2.297 g (7.28 mmol) of the Schiff base 7 was dissolved in 100 mL of ethanol, to which 0.19 g (5 mmol) of sodium borohydride was added portionwise. It was stirred at room temperature for 18 hours. The solvent was removed under reduced pressure to afforded 2.145 g of N-(2-hydroxy-5-nitrobenzyl), N'-(2-hydroxybenzyl)ethyl-enediamine, (8).

$^1$H NMR (in D$_2$O+NaOD): $\delta$7.67 (m,3H), 6.71 (t,J=7Hz, 1H), 6.15 (m,3H), 3.26 and 3.25 (2s,4H,—NH—CH$_2$—Ar) and 2.35 (s,4H, —NH—CH$_2$—CH$_2$—NH—) ppm.

Preparation of HBED-NO$_2$, (9)

(See Ref. 2) In a 50 mL round bottom flask, 360 mg (1.14 mmol) of the nitro diamine 8, 10 mL of water and 340 mg (2.45 mmol) of $\alpha$-bromo acetic acid were introduced. After 2 mL of 5.4 N sodium hydroxide was added, the reaction mixture was stirred at room temperature for 18 hours. The pH of the solution was lowered to about 4 with concentrated hydrochloric acid. The precipitate was filtered off, washed with water and ether and vacuum dried. 341 mg of N-(2-hydroxy- 5-nitrobenzyl), N'-(2-hydroxybenzyl)ethylenediamine-N,N'-diacetic acid (HBED-NO$_2$), C9) was obtained.

$^1$H NMR (in D$_2$O+NaOD): $\delta$ppm.

Preparation of HBED-SCN, (11)

A: Hydrogenation of the HBED-NO$_2$ (9)

(See Ref. 3) 233 mg (0.54 mmol) of HBED-NO$_2$ 9 dissolved in 20 mL of methanol and 57 mg of palladium on activated charcoal (5% Pd) was added. The mixture was hydrogenated at 47 psi for 195 min. The catalyst was filtered out on celite and the filtrate concentrated to about 2 mL. This HBED-NH$_2$ (10) solution was used immediately for the next reaction.

B: Formation of the isothiocyanate group

The above solution (HBED-NH$_2$) 10 was treated with a 0.21 N solution of thiophosgene in methylene chloride (2.43 mL; 0.51 mmol) and stirred under argon for 1 hour. The solution was then evaporated to dryness, giving N-(2-hydroxy-5-isocyanatobenzyl), N'-(2-hydroxybenzyl)ethylenediamine-N,N'-diacetic acid (HBED-SCN), 11 as a brownish powder (195 mg).

MS(API—MS; m/z): 446.1(M$^+$+1).

Preparation of HBED-Atrial Natriuretic Peptide R$^{ANP101-126}$ (5.0 mg), bicarbonate-/phosphate buffer (0.2 M, pH8.5,400 µL), DMSO (500 µL) and HBED-SCN (12.1 mg) 11 in DMSO (700 µL) were combined in a 5 mL round bottomed flask. The reaction mixture was stirred at room temperature for 20 hours followed by 6 hours at 38° C. The solvent was removed in vacuo and the residue dissolved in 10% acetic acid in water. Purification of the reaction mixture by HPLC (Partisil 5ODS(3) Phenomenex) using a gradient system (Solvent A: 0.1% TFA in acetonitfile, Solvent B: 0.1% TFA in water, T=0 min 20% A, 80% B, T=40 min 50% A, 50% B) afforded pure ANP-HBED. Unreacted ANP eluted at 10.5 minutes and the HBED-ANP elutes at 12.78 minutes.

MS(Electrospray, Hypermass) 828.0(z=4), 1103.4(z=3), 1654.8(z=2), Calc. Compound. Mass=3307.38, Meas. Compound Mass= 3307.58

Preparation of $^{111}$In-HBED-Atrial Natrimetic Peptide $^{111}$InCl$_3$ solution (10 µL Millex water>18 Mohms, 1 µL $^{111}$InCl$_3$) citrate buffer (20 µL, 0.01M, pH 7.6) and ANP-HBED (5 µg in 5 µL of Millex water) were placed in a 0.3 mL React-Vial. The mixture was incubated for 30 minutes and the progress of the reaction monitored by ITLC (Gelman-SG, 0.1M citrate as solvent). The crude reaction mixture was purified by chromatography using a PRP-1 solid-phase extractor (Hamilton & Co.). Elution of the PRP column with acetonitrile afforded pure $^{111}$In-HB ED-ANP.

SYNTHESIS OF HBPD-SCN

Preparation of N-(2-hydroxybenzyl), N'-acetylpropanediamine, (14)

A: N-Acetylpropanediamine (12)

(See Ref. 4 & 5) In a 1000 mL round bottom flask, 250 mL (222 g; 2.99 mole) of diaminopropane and 146 mL (131.69 g; 1.495 mole; 0.5 eq) of ethyl acetate were introduced. After this solution was heated at reflux for 24 hours, the reaction mixture was concentrated under reduced pressure. The residue was ditillated under vacuum to give 134.34 g of the N-acetylpropanediamine 12 as a colorless liquid.

$^1$H NMR (in CDCl$_3$): δ3.20 (td,J=6 and 8Hz,2H,—CH$_2$—NHCOCH$_3$), 2.65 (t,J=7Hz,2H,H$_2$N—$_3$CH$_2$—), 1.86 (s,3H,—NHCOCH$_3$), 1.74 (s,2H,—NH$_2$), 1.64 (quint, J=6Hz,1H,—NHCOCH$_3$), 1.52 (quint,J=7Hz,2H,—2CH$_2$—)ppm.

B: N-(2-Hydoxybenzylidene), N'-acetylpropanediamine, (13)

Salicycaldehyde 1, 6.11 g (0.05 mole), was dissolved in 25 mL of dry benzene. To this solution N-acetylethylenediamine 12, 5.808 g (0.05 mole), dissolved in 25 mL of dry benzene and few drops of methanol was slowly added. A Dean-Stark apparatus and a condenser were installed to the round bottom flask then the reaction mixture was heated to reflux for 48 hours. The solvent was removed under vacuum and the residue was washed with diethyl ether. After it was vacuum dried at room temperature and 0.1 mm Hg for 18 hours, 11.05 g of the yellow Schiff base 13 was obtained.

$^1$H NMR (in CDCl$_3$): δ8.23 (s,1H,—CH=N—), 7.20 (ddd,J=2, 7 and 8Hz, 1H,H$_4$—Ar), 7.14 (dd,J=2 and 8Hz, 1H,H$_6$—Ar), 6.83 (d,J=8Hz,1H,H$_3$—Ar), 6.77 (td,J=1 and 8Hz,1H,H$_5$—Ar), 6.18 (bs,1H,—NHCOCH$_3$), 3.51 (td,J=1 and 7Hz,2H,—CH=N—CH$_2$—CH$_2$—CH$_2$—NHCOCH$_3$), 3.22 (q,J=7Hz,2H, —CH=N—CH$_2$—CH$_2$—CH$_2$—NHCOCH$_3$), 1.85 (s,3H,—NHCOCH$_3$) and 1.79 (quint, J=7Hz, 2H,—CH=N—CH$_2$—CH$_2$—CH$_2$—NHCOCH$_3$)ppm. $^{13}$C NMR (in CDCl$_3$) 170.7, 165.9, 161.5, 132.8, 131.8, 119.1, 117.4, 57.7, 38.1, 31.3 and 23.8 ppm. MS (EI; m/z) 220(M$^+$,28), 221(M$^+$+1,19), 161 (20), 149(12), 148 (100), 134(25) 131(19), 121(12), 107(18), 43(11).

C: N-(2-Hydroxybenzyl), N'-acetylpropanediamine, (14)

11.05 g (0.05 mole) of the Schiff base 13 was dissolved in 50 mL of ethanol 99%, to which 0.991 g (0.026 mole) of sodium borohydride was added portionwise. It was stirred at room temperature for 24 hours. After the reaction mixture was cooled to room temperature, it was filtered and the solid was washed with cold ethanol. The filtrate was concentrated under reduced pressure to yield 12.13 g of N-(2-hydroxybenzyl), N'-acetylpropanediamine 14 as a light yellow oil.

$^1$H NMR (in CDCl$_3$): δ7.11 (t,J=7Hz,1H,H$_4$—Ar), 6.96 (d,J=7Hz,1H, H$_6$—Ar), 6.77 (d,J=9Hz, 1H,H$_3$—Ar), 6.72 (t,J=8Hz,1H,H$_5$—Ar), 6.14 (bs, 1H,—NHCOCH$_3$), 3.91 (s,2H,Ar—CH$_2$—NH—), 3.24 (q,J=6Hz,2H,—NH—(CH$_2$)$_2$—CH$_2$—NHCOCH$_3$), 2.61 (t,J=7Hz,2H,—NH—CH$_2$—(CH$_2$)$_2$—NHCOCH$_3$), 1.90 (s,3H, —NHCOCH$_3$) and 1.65 (quint,J=7Hz,1H,—NH—CH$_2$—CH$_2$—CH$_2$—NHCOCH$_3$)ppm.

Hydrolysis of N-(2-Hydroxybenzyl), N'-acetylpropanediamine, (14)

N-(2-hydroxybenzyl), N'-acetylpropanediamine 14 ( 12.13 g; 55 mmol) was dissolved in 200 mL of 6 N hydrochloric acid and this solution was refluxed for 21 ½ hours. After the solvent was evaporated under vacuum, the residue was dissolved with the minimum volume of water and the pH was brought to about 9 with 1 N sodium hydroxide. Then the mixture was extracted with ethyl acetate (3×200 mL). The combined extracts were dried with magnesium sulfate, filtered and evaporated to dryness to yield 8.9 g N-(2-hydroxybenzyl)propanediamine 15, of a brownish oil.

$^1$H NMR (in D$_2$O): δ6.87 (t,J=8Hz, 1H,H$_4$—Ar), 6.86 (d,J=8Hz,1H, H$_6$—Ar), 6.49 (d,J=8Hz,1H,H$_3$—Ar), 6.48 (t,J=7Hz,1H,H$_5$—Ar), 3.75 (s,2H, Ar—CH$_2$—NH—), 2.67 (t,J=8Hz,2H,Ar—CH$_2$—NH—CH$_2$—(CH$_2$)$_2$—NH$_2$), 2.61 (t, J=8.0Hz,2H, Ar—CH$_2$—NH—(CH$_2$)$_2$—CH$_2$—NH$_2$) and 1.64 (m,2H,—NH—CH$_2$—CH$_2$—CH$_2$—NH$_2$)ppm. MS (EI; m/z): 180(M$^+$,8), 181(M$^+$+1,14), 182(M$^+$+2,2), 179(17), 150(16), 148(10), 137(14), 136(28), 135(17), 134(15), 123(10), 122(47), 108(10), 107(100), 77(15), 73(12), 58(11), 44(30).

Preparation of N-(2-Hydroxy-5-nitrobenzyl), N'-(2-hydroxybenzyl) propanediamine, (17)

A: N-(2-Hydroxy-5-nitrobenzylidene), N'-(2-hydroxybenzyl)propane-diamine, (16)

N-(2-hydroxybenzyl)propanediamine 15, 1.07 g (4.2 mmol), was dissolved in 30 mL of dry benzene and 15 mL of methanol. To this solution 5-nitrosalicylaldehyde 6, 706 mg (4.23 mmol), dissolved in 25 mL of dry benzene and a few drops of methanol was slowly added. A Dean-Stark apparatus and a condenser were installed to the round bottom flask then the reaction mixture was refluxed for 43 hours. The solvent was removed under vacuum and the residue was washed with ether. After it was vacuum dried at room temperature and 0.1 mm Hg for 18 hours, and the Schiff base 16 was reduced without further purification.

B: N-(2-Hydroxy-5-nitrobenzyl), N'-(2-hydroxybenzyl) propane-diamine, (17)

1.38 g of the Schiff base 16 was dissolved in 100 mL of ethanol, to which 160 mg (4.2 mmol) of sodium borohydride was added portionwise. It was stirred at room temperature for 18 hours. The solvent was removed under reduced pressure to afforded 1.64 g of N-(2-hydroxy- 5-nitrobenzyl), N'-(2-hydroxybenzyl)propanediamine 17.

$^1$H NMR (in CDCl$_3$): δ8.09 (dd,J=3 and 9Hz, 1H,H$_4$—Ar—NO$_2$), 7.94 (d,J=3Hz,1H,H$_6$—Ar—NO$_2$), 7.17 (td,J=2 and 8Hz, 1H,H$_4$—Ar), 6.98 (d,J=7Hz,1H,H$_6$—Ar), 6.84 (d,J=9Hz, 1H,H$_3$—Ar—NO$_2$), 6.82 (d,J=7Hz,1H,H$_3$—Ar), 6.78 (td,J=1 and 7Hz,1H,H$_5$—Ar), 6.0 (bs,4H,—NH— and Ar—OH), 4.08 (s, 2H,—NH—CH$_2$—Ar—NO$_2$), 4.00 (s,2H,—NH—CH$_2$—Ar), 2.77 (t,J=7Hz,2H,—NH—$_1$CH$_2$—CH$_2$—CH$_2$—NH—), 2.77 (t,J=7Hz,2H,—NH—$_1$CH$_2$—CH$_2$—$_3$CH$_2$—NH—) and 1.81 (quint, J=7 Hz,2H,—NH—CH$_2$—CH$_2$—CH$_2$— NH—)ppm. $^{13}$C NMR (in CDCl$_3$) 158.1, 156.7, 130.7, 129.0, 128.6, 128.3, 122.8, 122.4, 119.1, 119.0, 118.9, 116.3, 115.9, 56.0, 52.5, 46.4, 39.8 and 32.3 ppm.

Preparation of HBPD-NO$_2$, (18)

(See Ref. 2) In a 50 mL round bottom flask, 341 mg( 1.03 mmol) of the nitro diamine 17, 7 mL of water and 310 mg (2.9 mmol) of α-bromo acetic acid were introduced. After 1.8 mL of 5.5 N sodium hydroxide was added, the reaction mixture was stirred at room temperature for 18 hours. The pH of the solution was lowered to about 4 with 6 N hydrochloric acid. After the solution was dried under vacuum, the solid was dissolved with methanol and filtered. The solvent was evaporated under reduced pressure and the residue was purified by flash chromatography (CHCl$_3$ with 30% of methanol) to give 650 mg of N-(2-hydroxy- 5-nitrobenzyl), N'-(2-hydroxybenzyl)propanediamine-N,N'-diacetic acid (HBPD-NO$_2$), (18) was obtained.

$^1$H NMR (in D$_2$O): δ ppm.

Preparation of HBPD-SCN. (20)

A: Hydrogenation of the HBPD-NO$_2$, (18)

After 121 mg (0.27 mmol) of HBPD-NO$_2$ 18 was dissolved in 45 mL of methanol and 10 drops of 0.1 N sodium hydroxyde, 57 mg of palladium on activated charcoal (10% Pd) was added. The mixture was hydrogenated at 39 psi for 24 hours. The catalyst was filtered out on celite and the tiltrate concentrated to about 2 mL. This HBPD-NH$_2$ (19) solution was used immediately for the next reaction.

B: Formation of the isothiocyanate group

The above solution (HBPD-NH$_2$ 19) was treated with a 0.21 N solution of thiophosgene in methylene chloride (1.31 mL; 0.27 mmol) and stirred under argon for 1 hour. The solution was then evaporated to dryness, giving N-(2-hydroxy-5-isocyanatobenzyl), N'-(2-hydroxybenzyl)propanediamine-N,N'-diacetic acid (HBPD-SCN), 20 as a brownish powder (133 mg).

MS(API-MS; m/z):460.1(M$^+$+1).

Synthesis Of HTDD-SCN

Preparation of bis(2'-Phthalimidoethyl)amine[6], (23)

Phthalic anhydride (32 g; 0.22 mol) was dissolved in 333 mL of hot chloroform and the mixture was filtered to eliminate phthalic acid*. A Diethylenetriamine (7.97 g; 0.077 mol) solution in chloroform (64 mL) was slowly added (over a period of 50 minutes) to the phthalic anhydride mixture maintained at a temperature of 50° C. Temperature was raised to 110° C. after the addition was over. The reaction mixture was then stirred for 48 hours and slowly concentrated. The concentrate solution was then treated with activated charcoal. 31.8 g of a yellow solid was recovered after evaporation of the solvent under reduced pressure. The solid was triturated successively with ether, ethanol and then dissolved in methylene chloride. The methylene chloride solution was washed with 10% sodium carbonate (3×500 mL), water and saturated sodium chloride solution. The organic phase was dried with magnesium sulfate, filtered and evaporated to dryness under reduced pressure. A pale yellow solid (14.47 g; 52%) was obtained. A portion (4.45 g) of that product was purified by flash chromatography (silica gel) using a mixture of methylene chloride, ethyl acetate and triethylamine as elution system (79/20/1). The purification give 2.798 g of bis (phthalimidoethyl)amine (23).

* 6.96 g of phthalic acid was recovered.

$^1$H NMR (in CDCl$_3$): δ7.70 (m,8H,H—Ar(phth)), 3.77 (t,J=6Hz,4H,—NH(—CH$_2$—CH$_2$—NPhth)$_2$), 2.95 (t,J=6Hz,4H,—NH(—CH$_2$—CH$_2$—NPhth)$_2$), 1.41 (broad, 1H,—NH(—CH$_2$—CH$_2$—NPhth)$_2$)ppm. IR (in CDCl$_3$/ NaCl): 3460 (N—H,w, sec amine), 2940–2820 (C—H), 1770–1710 (C=O, Phth), 1465, 1425, 1390, 1360, 1185, 1035 cm$^{-1}$. MS (EI; m/z): 363(0.4,M$^+$), 364(4,M$^+$+ 1), 216(3,M$^+$—Phth), 204(18), 203(100,M$^+$—(Phth—CH$_2$·)), 174(57,Phth—CH$_2$—CH$_2^+$), 160(5), 147(6), 130(12) and 56(6).

Preparation of N'-(4-Nitrobenzyl) bis(2'-phtalimidoethyl)amine (23)

(See Ref. 7) In a 250 mL round bottom flask potassium hydroxyde (1.6 g; 28 mmol) was dissolved in hot ethanol (100 mL). To that ethanolic solution Bis(2'-phthalimidoethyl)amine (2.3) (10.02 g; 28 mmol) was added. The solution was magnetically stirred and refluxed for 2½ hours before p-nitrobenzyl bromide (5.95 g; 28 mmol; 1 eq) was added. The reaction mixture was heated at reflux for 16 additional hours then filtered hot. The solid obtained previously was washed with absolute ethanol and dried under vacuum to yield 7.441 g (54%) of a white solid (p-nitrobenzyl bisphthalimide). The filtrate was evaporated under reduced pressure to give 8.19 g of a yellow solid. That residue was purified by flash chromatography (silica gel: 400 g) using methylene chloride-methanol (98/2) system as eluent. The purification by chromatography produced 3.13 g (23%) of the desired product. The alkylation reaction yielded 10.571 g of N'-(4-nitrobenzyl) bis(2'-phtalimidoethyl)amine (24).

$^1$H NMR (in CDCl$_3$): δ7.70 (m,10H,H—Ar(Phth)+ o(H)—Ar—NO$_2$), 7.20 (d, J=9Hz,2H, m(H)—Ar—NO$_2$), 3.75 (t, J=6Hz, 4H,—NH (—CH$_2$—CH$_2$—NPhth)$_2$), 3.71 (s, 2H,—N—CH$_2$—Ar—NO$_2$) and 2.80 (t, J=6Hz,4H,—NH(—CH$_2$—CH$_2$—NPhth)$_2$)ppm. MS (EI; m/z): 498(1,M$^+$), 499(0.6,M$^+$+1), 362(1,M$^+$—·CH$_2$Ar—NO$_2$), 339 (32, M$^+$+1—(Phth—CH$_2$·)), 338 ( 100, M$^+$—(Phth—CH$_2$·)), 324 (2, M$^+$—(Phth—CH$_2$—CH$_2$·)), 174(58,Phth—CH$_2$—CH$_2^+$), 173(42), 165(6), 163 (8), 161(6), 160 (43), 149(12), 136(24), 130(12), 106(21), 105(12), 104(17), 90(22), 89 (18), 78(23), 77(21) and 76(12).

Hydrolysis of N'-(4-Nitrobenzyl) bis(2-phtalimidoethyl)amine (24)

In a 250 mL round bottom flask, provided with a condenser, N'-(4-nitrobenzyl) bis(2'-phtalimidoethyl)amine (24) (2.80 g; 5.62 mmol) and 6 N hydrochloric acid (150 mL) were introduced. The reaction mixture was stirred and refluxed for 23 hours. The solution was cooled with an ice bath and filtered. The flitrate was washed with ether (3×100 mL) and dried by vacuum to give a yellow foam-like material (2.17 g). The residue was dissolved in water (10 mL) and the pH of that solution was brought basic with 1 N sodium hydroxide (25 mL). Then the mixture was extracted with methylene chloride (3×75 mL). The organic extracts were combined, dried with magnesium sulfate, filtered and evaporated to dryness to yield 1.347 g of N'-(4-nitrobenzyl) bis(2'-aminoethyl)amine (25) as a light orange oil (which turn dark red with time).

Note: The p-nitrobenzyltriamine (25) is stored for short term away from light and in an inert atmosphere of argon. For long term storage it is better to keep that compound as the hydrochlorate form.

$^1$H-NMR (in CDCl$_3$): δ8.13 (d,J=9Hz,2H,o(H)—Ar—NO$_2$), 7.46 (d, J=9Hz, 2H,m(H)—Ar—NO$_2$), 3.65 (s,2H,—N—CH$_2$—Ar—NO$_2$), 2.74 (t,J=6Hz, 4H, —N(—CH$_2$—CH$_2$—NH$_2$)$_2$), 2.50 (t,J=6Hz,4H,—N(—CH$_2$—CH$_2$—NH $_2$)$_2$) and 1.43 (broad s, 4H,—N(—CH$_2$—CH$_2$—NH$_2$)$_2$)ppm. IR (film): 3370–3290 (N—H,—NH$_2$), 2940–2800(C—H), 1605 (C=C,Ar), 1510 (N=O,Ar), 1450, 1340 (N=O,Ar), 1105, 1010, 850 (C—N,Ar—NO$_2$) and 730 cm$^{-1}$.

Preparation of N,N"-Bis[2'-(2"-hydroxybenzyl)aminoethyl]N'-(4-nitrobenzyl)amine (27)

A: N,N"-Bis[ 2'-(2"-hydroxybenzylidene)aminoethyl] N'-(4-nitrobenzyl)amine (26)

Salicylaldehyde 1 (233.8 mg; 1.91 mmol; 2.02 eq) was dissolved in 140 mL of dry benzene. To this solution N'-(4-nitrobenzyl) bis(2'-aminoethyl)amine (25) (226.4 mg; 0.95 mmol) dissolved in 20 mL of dry benzene was slowly added. A Dean-Stark apparatus and a condenser were installed to the round bottom flask then the reaction mixture was heated to reflux for 41 hours. The solvent was removed under vacuum to produce 416 mg of the Schiff base 26 as red oil.

$^1$H NMR (in CDCl$_3$): δ8.22 (s,2H, HO—Ar—CH=N—), 7.98 (d, J=9Hz, 2H,o(H)—Ar—NO$_2$), 7.37 (d,J=9Hz,2H, m(H)—Ar—NO$_2$), 7.31 (ddd,J=1.5, 7 and 8Hz,2H,$_5$H—Ar—OH), 7.04 (dd,J=2 and 8Hz,2H,$_6$H—Ar—OH), 6.94 (d, J=8Hz,2H,$_3$H—Ar—OH), 6.83 (ddd,J=1, 7 and 8Hz, $_4$H— Ar—OH), 3.79 (s, 2H,—N—CH$_2$—Ar—NO$_2$), 3.67 (t, J=6Hz,4H,—N(—CH$_2$—CH$_2$—N=CH—)$_2$) and 2.91 (t,J=6Hz,4H,—N(—CH$_2$—CH$_2$—N=CH—)$_2$)ppm. IR (film): 3060, 2940–2840 (C—H), 1635 (C=N), 1605(C=C,Ar), 1580, 1515 (N=O,Ar), 1495, 1460, 1345 (N=O,Ar), 1275, 1145, 850 (C—N,Ar—NO $_2$), 750 and 730 cm$^{-1}$. MS (EI; m/z): 446(9,M$^+$), 447(4,M$^+$+1), 429(12, M$^+$—HO·), 338(11 ), 326(5,M$^+$—(HO—Ar—CH=N·)), 325(24), 313(21), 312(100,M$^+$—(HO—Ar—CH=N—

$CH_2$·)), 206(34), 177(38), 148(15), 135(12), 134(18), 107(29), 106(10), 78(12) and 77(14).

B: N,N''-Bis[2'-(2''-hydroxybenzyl)aminoethyl]N'-(4-nitrobenzyl)amine (27)

The Schiff base 26 (399.8 mg; 0.9 mmol) was dissolved in a mixture of methanol (20 mL) and benzene (20 mL). Sodium borohydride (73.5 mg; 1.94 mmol) was added portionwise to that solution and the reaction medium was stirred at room temperature for 17 hours. The solvent was removed under reduced pressure. To the remaining residue was added 50 mL of water and the product was extracted four times with methylene chloride (50 mL). The organic extracts (green color) were combined and decolorized with 150 mg of activated charcoal. The mixture was warmed for 10 min. After filtration a light yellow methylene chloride solution was obtained. This solution was dried with anhydrous magnesium sulfate, filtered and the solvent removed under reduced pressure to yield 346 mg of N,N''-bis[2'-(2''-hydroxybenzyl)aminoethyl]N'-(4-nitrobenzyl) amine (27) as a light yellow oil. That crude compound was purified by flash chromatography (silica gel) using methylene chloride-methanol-ammonium hydroxide (94.5/5/0.5) system as eluent. The purification by chromatography produced 296 mg (2 steps: 73%) of the desired N,N''-bis[2'-(2''-hydroxybenzyl)aminoethyl]N'-(4-nitrobenzyl) amine (27).

$^1$H NMR (in $CDCl_3$): δ8.18 (d,J=9Hz,2H,o(H)—Ar—$NO_2$), 7.47 (d,J=9Hz,2H,m(H)—Ar—$NO_2$), 7.16 (dr,J=2 and 8Hz,2H,$_5$H—Ar—OH), 6.93 (d,J=7Hz, 2H, $_3$H—At—OH), 6.79 (d, J=8 Hz, 2H, $_6$H—Ar—OH), 6.77 (t, J=7Hz, 2H, $_4$H—Ar—OH), 3.93 (s,4H,—NH—$CH_2$—Ar—OH), 3.68 (s,2H,—N—$CH_2$—Ar—$NO_2$), 2.73 (t, J=5 Hz,4H,—N(—$CH_2$—$CH_2$—NH—)$_2$) and 2.63 (t,J=5 Hz,4H,—N(—$CH_2$—$CH_2$—N—)$_2$)ppm. MS (EI; m/z): 451 (1, $M^+$+1), 338 (1), 327 (2,$M^+$—1—$CH_2$—Ar—$NO_2$), 314(4), 208(29), 193(9), 192(17), 180(11), 179(23), 149(11), 136(45), 108(12), 107(100,+$CH_2$—Ar—OH), 106(40), 94(24), 90(16), 78(31), 77(230, 73(22), 66(19), 44(40).

Preparation of the Dibenzyl ester of HTDD-$NO_2$ (28)

In a 100 mL round bottom flask, 258 mg (0.57 mmol) of the p-nitrobenzyl triamine 27, 30 mL of ethanol, 15 mL of methylene chloride and 30 μL (434 mg; 1.89 mmol; 3.3 eq) of benzyl α-bromo acetate were introduced. The reaction mixture was stirred at reflux in an inert atmosphere of argon for 44½ hours. The solution was concentrated under vacuum to give 698 mg of a brown oil which was then purified by flash chromatography ($CH_2Cl_2$: MeOH:Hexane; 47.5/2.5/50 (500 mL) raised the ploarity to 63.7/3.3/33 (500 mL) then 71.3/3.7/25 (500 mL)). From the purification two compounds were isolated. The first (98 mg) is the desired dialkylated product (N,N''-dicarbobenzyloxy N,N''-bis[2'-(2''-hydroxybenzyl)aminoethyl] N'-(4-nitrobenzyl) amine 28) and the second (84 mg) a monoalkylated product (N-carbobenzyloxy N,N''-bis[2'-(2''-hydroxybenzyl)aminoethyl] N'-(4-nitrobenzyl)amine 29). A fraction (59 mg) containing a mixture of the two compounds (28 and 29) has also been recovered.

N,N''-Dicarbobenzyloxy N,N''-bis[2'-(2''-hydroxybenzyl)aminoethyl] N'-( 4-nitrobenzyl) amine 28

$^1$H NMR (in $CDCl_3$): δ9.75 (s, 2H, Ar—OH), 8.03 (d, J=9Hz, 2H, o(H)Ar—$NO_2$), 7.33 (m,12H,—$CO_2$—$CH_2$—$C_6H_5$ and m(H)Ar—$NO_2$), 7.17 (td,J=2 and 7Hz,2H,$_5$H—Ar—OH), 6.89 (dd,J=2 and 7Hz,2H,$_3$H—Ar—OH), 6.83 (d,J=7Hz,2H,$_6$H—Ar—OH), 6.74 (td,J=1 and 7Hz,2H,$_4$H—Ar—OH), 5.12 (s,4H,—$CO_2$—$CH_2$—$C_6H_5$), 3.71 (s,4H,—N—$CH_2$— Ar—OH), 3.52 (s,2H,—N—$CH_2$—Ar—$NO_2$), 3.30 (s,4H,—N—$CH_2$—$CO_2$Bn), 2.68 (t,J=6Hz,4H,—N—$CH_2$—$CH_2$—N—$CO_2$Bn) and 2.54 (t, J=6Hz,4H,—N—$CH_2CH_2$—N—$CO_2$Bn)ppm. IR (film): 3340(broad, O—H, phenol), 3060–3030(C—H, Ar), 2950–2815 (C—H), 1740 (C=O, ester), 1620, 1605, 1590, 1520( N=O, Ar), 1490, 1345 (N=O, Ar), 1250, 1180, 1090, 1035, 960, 850, 750, 695 $cm^{-1}$.

N-Carbobenzyloxy N,N''-bis[2'-(2''-hydroxybenzyl)aminoethyl]N'-(4-nitrobenzyl)amine 29

$^1$H NMR (in $CDCl_3$): δ8.12 (d,J=9Hz,2H,o(H)Ar—$NO_2$), 7.42 (d,J=9Hz,2H,m(H)Ar—$NO_2$), 7.34(broad s,5H,—$CO_2$—$CH_2$—$C_6H_5$), 7.17 and 7.14 (2 td,J=2 and 7Hz,2H,$_5$H—Ar—OH), 6.91 (t,J=8Hz,2H,$_3$H— Ar—OH), 6.78 (m,4H, H—Ar—OH), 5.13 (s,2H,—$CO_2$—$CH_2$—$C_6H_5$), 3.85 (s,2H,—N—$CH_2$—Ar—OH), 3.78 (s,2H,—N—$CH_2$—Ar—OH), 3.62 (s,2H,—N—$CH_2$— Ar—$NO_2$), 3.33 (s,2H,—N—$CH_2$—$CO_2$Bn), 2.75 (t,J=6Hz,2H,—N—$CH_2$—$CH_2$— N—$CO_2$Bn) and 2.59 (m,6H,—N—$CH_2$—$CH_2$—N—$CO_2$ Bn+—N—$CH_2$—$CH_2$—N—$CO_2$Bn)ppm.

Preparation of HTDD-SCN, (31)

A. Catalytic hydrogenation of N,N''-Dicarbobenzyloxy N,N''-bis[2'-(2'-hydroxybenzyl)aminoethyl]N'-(4-nitrobenzyl)-amine (26)[8,9]

In a Parr hydrogenation bottle, the dibenzyl ester of HTDD-$NO_2$ 28 (91 mg; 0.12 mmol), methanol (12.5 mL), ethyl acetate (12.5 mL) and 10% palladium on activated charcoal (40 mg) were introduced. The mixture was hydrogenated at 42 psi for 7 hours. The catalyst was filtered out on celite and the tiltrate concentrated to dryness to give 66 mg of the HTDD-$NH_2$ 30 as a yellow oil.

B: Formation of the isothiocyanate group

A methanolic solution of HTDD-$NH_2$ 30 (65 mg; 0.12 mmol/5 mL) was treated with a 0.21 N solution of thiophosgene in methylene chloride (0.65 mL; 0.134 mmol; 1.11 eq) and stirred under argon for 72 minutes. The solution was then evaporated to dryness under vacuum, giving N,N''-dicarboxy N,N''-bis[2'-(2''-hydroxy-benzyl)aminoethyl]N'-(4-isocyanatobenzyl)amine (HTDD-SCN), 31 as a pale yellow solid (85 mg).

Preparation of HTDD-Atrial Natriuretic Peptide

In a 5 mL Reacti-Vial (Pierce) a solution of $_R$ANP$^{101-126}$ 31 (3.51 mg; 1.2 μmol) and bicarbonate/phosphate buffer (0.2 M, pH 9.2, 1200 μL) was prepared and stirred for 10 minutes before use. In an another 5 mL Reacti-Vial (Pierce) HTDD-SCN (11.95 mg; 20.7 μmol, 17 eq) was introduced followed by the addition of the ANP solution previously prepared. The first Reacti-Vial was rinsed three times with a total of 1000 μL of the buffer which was afterward added to the mixture to give a final volume of 2200 μL (ANP conc.: 1.6 μg/μL; 0.55 mM, HTDD-SCN conc.: 5.4 μg/μL; 9 mM). The reaction mixture was stirred at room temperature and monitored by HPLC (until the complete disappearance of ANF peak). After 18 hours an additional 200 μL of buffer and 410 μg of HTDD-SCN were added and the mixture was stirred for 8 more hours. The reaction mixture was centrifuged at 5000 rpm for 5 minutes and the supernatant was removed (JMD-III-12-A). Methanol (1.5 mL) was the added to the solid residue and then stirred for 30 minutes. The mixture was centrifuged at 5000 rpm for 10 minutes and the supernatant was removed. The same process was repeated three more times and the methanolic solutions were combined (JMD-III-112-B). Water (1.5 mL) and hydrochloric acid 1 N (200 μL) was the added to the solid residue and then stirred for 30 minutes (JMD-III-112-C). The three solutions (IMD-III-112 A, B and C) were analyzed by HPLC (Hamilton PRP-I 10μ analytical column 250×4.1 mm) using a 10 to 50% gradient of acetonitrile (containing 0.1% TFA) in 40 minutes (flow rate of 1 mL/min). The solution JMD-III-112-C showed the presence of a new product (ANP-HTDD)

with a retention time ($R_T$) of 24.45 minutes and a small quantity of ANP ($R_T$=21.88 min). Purification of that solution (C) by HPLC (Hamilton PRP-I 10 µg preparative column 250×21.5 mm) using a 10 to 40% gradient of acetonitrile (containing 0.1% TFA) in 40 minutes (flow rate of 12 mL/min) afforded pure ANP-HTDD ($R_T$=30.99 min).

MS (Electrospray, Hypermass) 689.2(z=5), 861.29(z=4), 47.9 (z=3), Calc. Compound Mass=3440.7, Meas. Compound Mass=3441.1 g/mole.

1. Carla J. Mathias, Y. Sun, J. M. Connett, G. W. Philpott, M. J. Welch and Arthur E. Martell, *Inorg. Chem.*, 29, 1475–1480 (1990).
2. D. A. Westerberg, P. L. Camey, P. E. Rogers, S. J. Kline and D. K. Johnson, *J. Med. Chem.*, 32, 236–243 (1989).
3. John F. W. Keena and Jeffry S. Mann, *J. Org. Chem.*, 55, 2868–2871 (1990).
4. G. McLendon, R. J. Motekaitis and A. E. Martell, *Inorg. Chem.*, 14 (8), 1993–1996 (1975).
5. P. W. Erhardt, C. H. Woo, W. L. Matier, R. J. Gorczynski and W. G. Anderson, *J. Med. Chem.*, 26, 1112–1116 (1983).
6. Graeme H. Searle, S. F. Lincoln, S. G. Teague and D. G. Rowe, *Aust. J. Chem.*, 32, 519–536 (1979).
7. M. R. A. Pillai, J. M. Lo, C. S. John and D. E. Troutner, *Nucl. Med. Biol.*, 17 (4), 419–426 (1990).
8. Paul N. Rylander, *Catalytic hydrogenation in Organic Synthesis,* Academic Press, New York, 64–65 and 113–137 (1979).
9. Paul N. Rylander, *Catalytic hydrogenation over platinum metals,* Academic Press, New York, 168–202 (1967).

What is claimed is:

1. A compound of the structure:

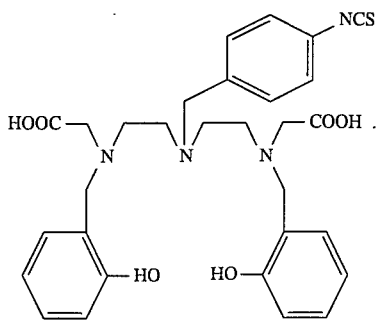

* * * * *